(12) United States Patent
McDaniel et al.

(10) Patent No.: US 8,007,495 B2
(45) Date of Patent: Aug. 30, 2011

(54) CATHETER FOR CIRCUMFERENTIAL ABLATION AT OR NEAR A PULMONARY VEIN

(75) Inventors: Benjamin D. McDaniel, Corona del Mar, CA (US); Dean M. Ponzi, Glendora, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 198 days.

(21) Appl. No.: 10/816,396

(22) Filed: Mar. 31, 2004

(65) Prior Publication Data
US 2005/0222563 A1    Oct. 6, 2005

(51) Int. Cl.
*A61B 18/14* (2006.01)
(52) U.S. Cl. .......................................... 606/41; 607/101
(58) Field of Classification Search ............... 606/41–50; 607/101–102, 122
See application file for complete search history.

(56) References Cited

U.S. PATENT DOCUMENTS

| | | | |
|---|---|---|---|
| 4,203,430 A | 5/1980 | Takahashi | |
| 4,207,873 A | 6/1980 | Kruy | |
| 4,699,147 A * | 10/1987 | Chilson et al. | 600/374 |
| 4,777,955 A | 10/1988 | Brayton et al. | |
| 4,882,777 A | 11/1989 | Narula | |
| 4,920,980 A | 5/1990 | Jackowski | |
| 4,960,134 A * | 10/1990 | Webster, Jr. | 607/116 |
| 4,984,581 A | 1/1991 | Stice | |
| 5,170,787 A | 12/1992 | Lindegren | |
| 5,255,679 A | 10/1993 | Imran | |
| 5,263,493 A | 11/1993 | Avitall | |
| 5,275,162 A | 1/1994 | Edwards et al. | |
| 5,304,214 A | 4/1994 | DeFord et al. | |
| 5,327,905 A | 7/1994 | Avitall | |
| 5,354,297 A | 10/1994 | Avitall | |
| 5,383,923 A | 1/1995 | Webster, Jr. | |
| 5,395,332 A | 3/1995 | Ressemann et al. | |
| 5,411,025 A | 5/1995 | Webster, Jr. | |
| 5,445,148 A | 8/1995 | Jaraczewski et al. | |
| 5,456,664 A | 10/1995 | Heinzelman et al. | |
| 5,471,982 A * | 12/1995 | Edwards et al. | 600/374 |
| 5,487,385 A | 1/1996 | Avitall | |
| 5,540,649 A | 7/1996 | Bonnell et al. | |
| 5,545,200 A | 8/1996 | West et al. | |
| 5,549,581 A | 8/1996 | Lurie et al. | |
| 5,575,772 A | 11/1996 | Lennox | |

(Continued)

FOREIGN PATENT DOCUMENTS

EP    0 499 491 A2    8/1992

(Continued)

*Primary Examiner* — Michael Peffley
(74) *Attorney, Agent, or Firm* — Christie, Parker & Hale, LLP

(57) ABSTRACT

A catheter has a three-dimensional, hollow ablation assembly that carries at least one ribbon electrode for circumferential ablation. In one embodiment, the assembly has a free-form framework that is constructed of multiple tensile members or wires that are interwoven such that the length of the framework increases while the circumference of the framework decreases, and vice versa. The assembly can also have a self-expanding stent-type framework which is mounted on the expander. In another alternative embodiment, the framework is a tubular or cylindrical structure whose side wall has longitudinal slots between longitudinal slats for radial expansion to a greater circumference when the length is decreased. The flexible ribbon electrode on the assembly is elastic, or is pleated so that it folds when the framework is collapsed and unfolds when the framework is deployed.

24 Claims, 11 Drawing Sheets

U.S. PATENT DOCUMENTS

| | | | |
|---|---|---|---|
| 5,582,609 A | | 12/1996 | Swanson et al. |
| 5,617,854 A | | 4/1997 | Munsif |
| 5,626,136 A | | 5/1997 | Webster, Jr. |
| 5,628,313 A | | 5/1997 | Webster, Jr. |
| 5,642,736 A | | 7/1997 | Avitall |
| 5,656,030 A | | 8/1997 | Hunjan et al. |
| 5,673,695 A | | 10/1997 | McGee et al. |
| 5,680,860 A | | 10/1997 | Imran |
| 5,730,127 A | | 3/1998 | Avitall |
| 5,755,760 A | | 5/1998 | Maguire et al. |
| 5,772,590 A | * | 6/1998 | Webster, Jr. .................. 600/374 |
| 5,782,239 A | | 7/1998 | Webster, Jr. |
| 5,782,760 A | | 7/1998 | Schaer |
| 5,782,899 A | | 7/1998 | Imran |
| 5,797,905 A | | 8/1998 | Fleischman et al. |
| 5,800,428 A | | 9/1998 | Nelson et al. |
| 5,823,955 A | | 10/1998 | Kuck et al. |
| 5,827,278 A | | 10/1998 | Webster, Jr. |
| 5,836,947 A | | 11/1998 | Fleischman et al. |
| 5,860,920 A | | 1/1999 | McGee et al. |
| 5,860,974 A | * | 1/1999 | Abele ............................ 606/41 |
| 5,865,800 A | | 2/1999 | Mirarchi et al. |
| 5,879,295 A | | 3/1999 | Li et al. |
| 5,882,333 A | | 3/1999 | Schaer et al. |
| 5,882,346 A | | 3/1999 | Pomeranz et al. |
| 5,899,860 A | | 5/1999 | Pfeiffer et al. |
| 5,931,811 A | | 8/1999 | Haissaguerre et al. |
| 5,935,102 A | | 8/1999 | Bowden et al. |
| 5,938,694 A | | 8/1999 | Jaraczewski et al. |
| 5,951,471 A | | 9/1999 | de la Rama et al. |
| 5,984,909 A | | 11/1999 | Lurie et al. |
| 5,997,526 A | | 12/1999 | Giba et al. |
| 6,002,955 A | | 12/1999 | Willems et al. |
| 6,035,224 A | | 3/2000 | West |
| 6,064,902 A | | 5/2000 | Haissaguerre et al. |
| 6,064,905 A | | 5/2000 | Webster, Jr. et al. |
| 6,088,614 A | | 7/2000 | Swanson |
| 6,090,104 A | | 7/2000 | Webster, Jr. |
| 6,096,036 A | | 8/2000 | Bowe et al. |
| 6,102,908 A | | 8/2000 | Tu et al. |
| 6,106,522 A | | 8/2000 | Fleischman et al. |
| 6,117,101 A | * | 9/2000 | Diederich et al. .............. 604/22 |
| 6,123,699 A | | 9/2000 | Webster, Jr. |
| 6,129,724 A | | 10/2000 | Fleischman et al. |
| 6,146,381 A | | 11/2000 | Bowe et al. |
| 6,162,219 A | | 12/2000 | Nilsson et al. |
| 6,163,716 A | | 12/2000 | Edwards et al. |
| 6,169,916 B1 | | 1/2001 | West |
| 6,171,277 B1 | | 1/2001 | Ponzi |
| 6,183,435 B1 | | 2/2001 | Bumbalough et al. |
| 6,183,463 B1 | * | 2/2001 | Webster, Jr. .................. 604/528 |
| 6,198,974 B1 | | 3/2001 | Webster, Jr. |
| 6,210,407 B1 | | 4/2001 | Webster |
| 6,219,582 B1 | | 4/2001 | Hofstad et al. |
| 6,261,246 B1 | | 7/2001 | Pantages et al. |
| 6,292,695 B1 | | 9/2001 | Webster, Jr. et al. |
| 6,325,797 B1 | | 12/2001 | Stewart et al. |
| 6,514,249 B1 | * | 2/2003 | Maguire et al. ................. 606/41 |
| 6,547,788 B1 | | 4/2003 | Maguire et al. |
| 6,741,878 B2 | | 5/2004 | Fuimaono et al. |
| 6,826,420 B1 | * | 11/2004 | Beatty et al. .................. 600/374 |
| 6,837,886 B2 | * | 1/2005 | Collins et al. .................... 606/41 |
| 7,371,232 B2 | | 5/2008 | Scheib |
| 2002/0165535 A1 | | 11/2002 | Lesh et al. |
| 2003/0195508 A1 | | 10/2003 | Scheib |

FOREIGN PATENT DOCUMENTS

| | | |
|---|---|---|
| EP | 0 928 601 A1 | 7/1999 |
| EP | 0 985 423 A2 | 3/2000 |
| WO | WO 01/74255 A1 | 10/2001 |

* cited by examiner

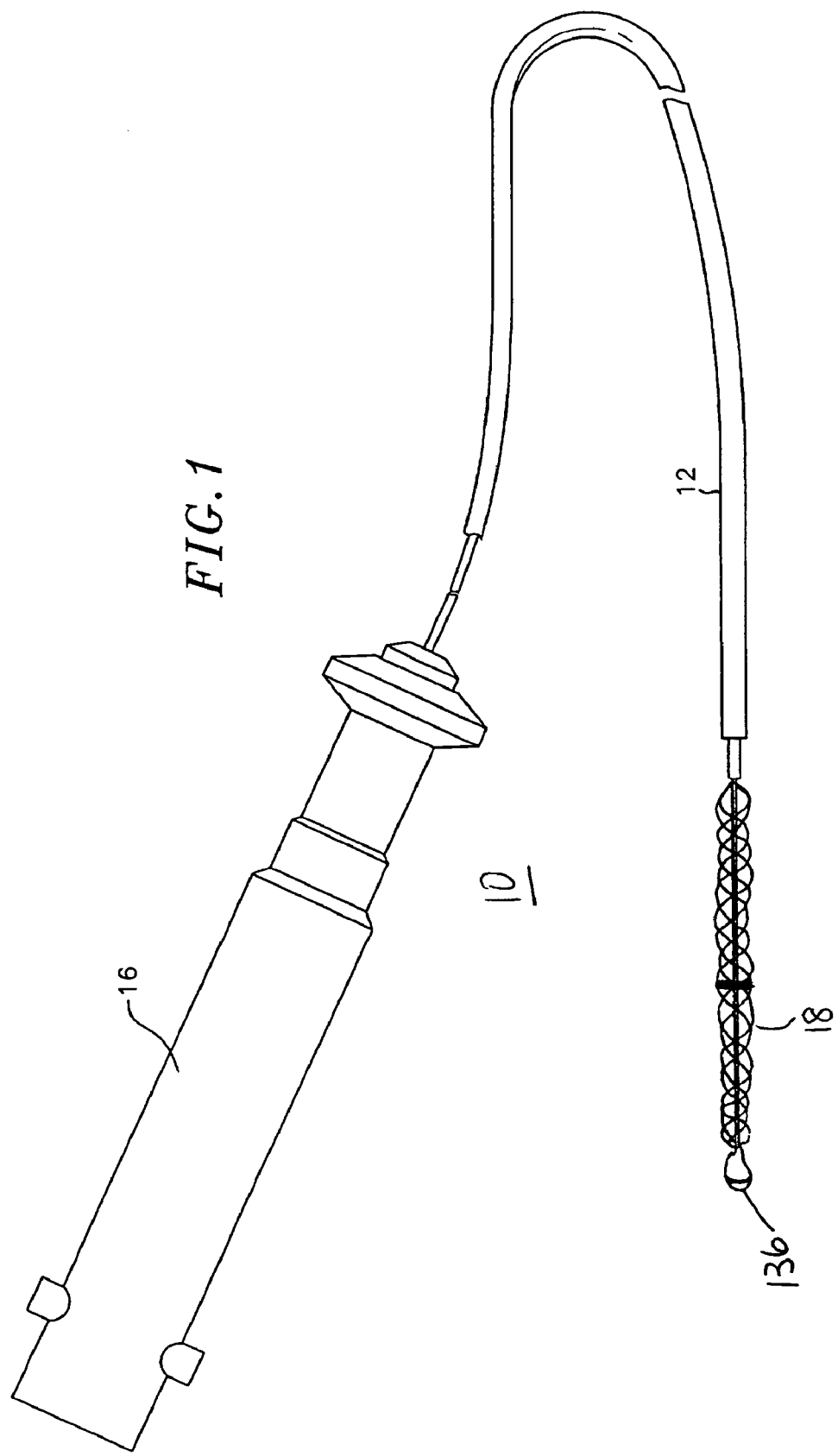

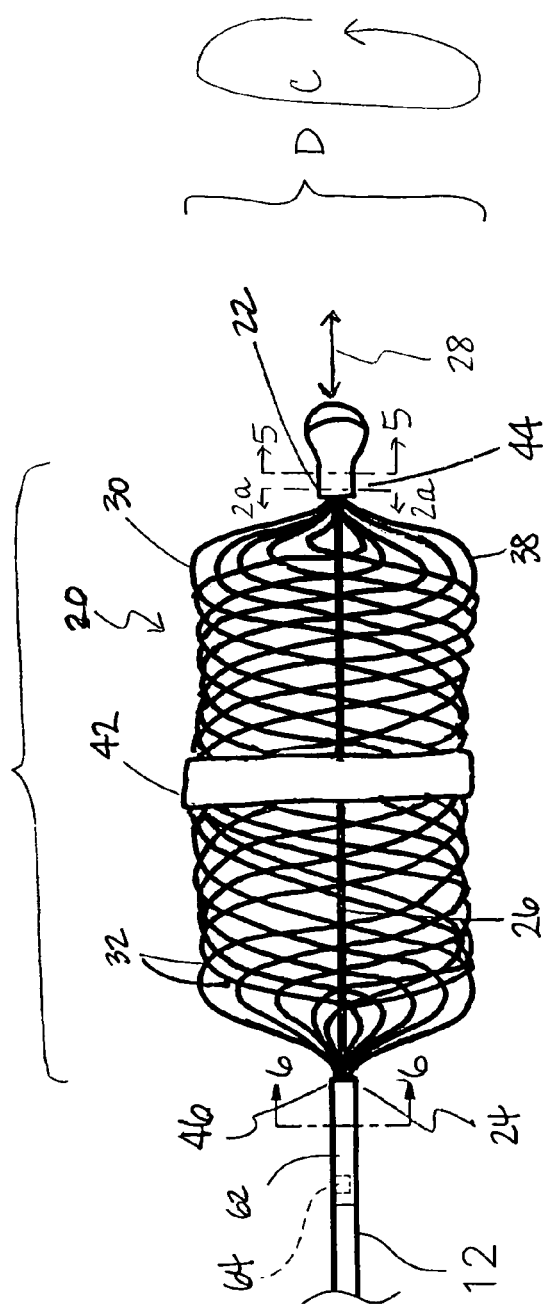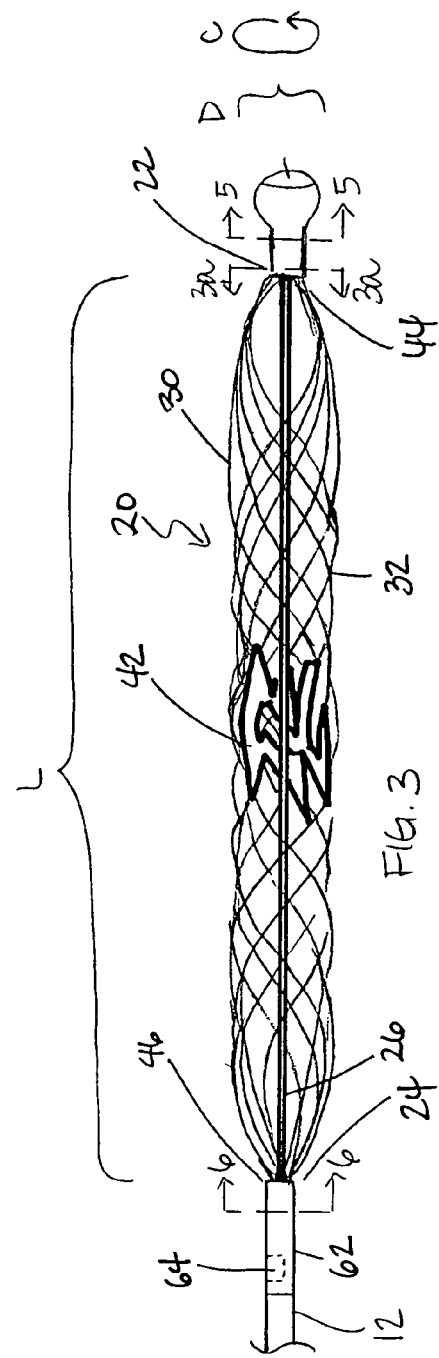

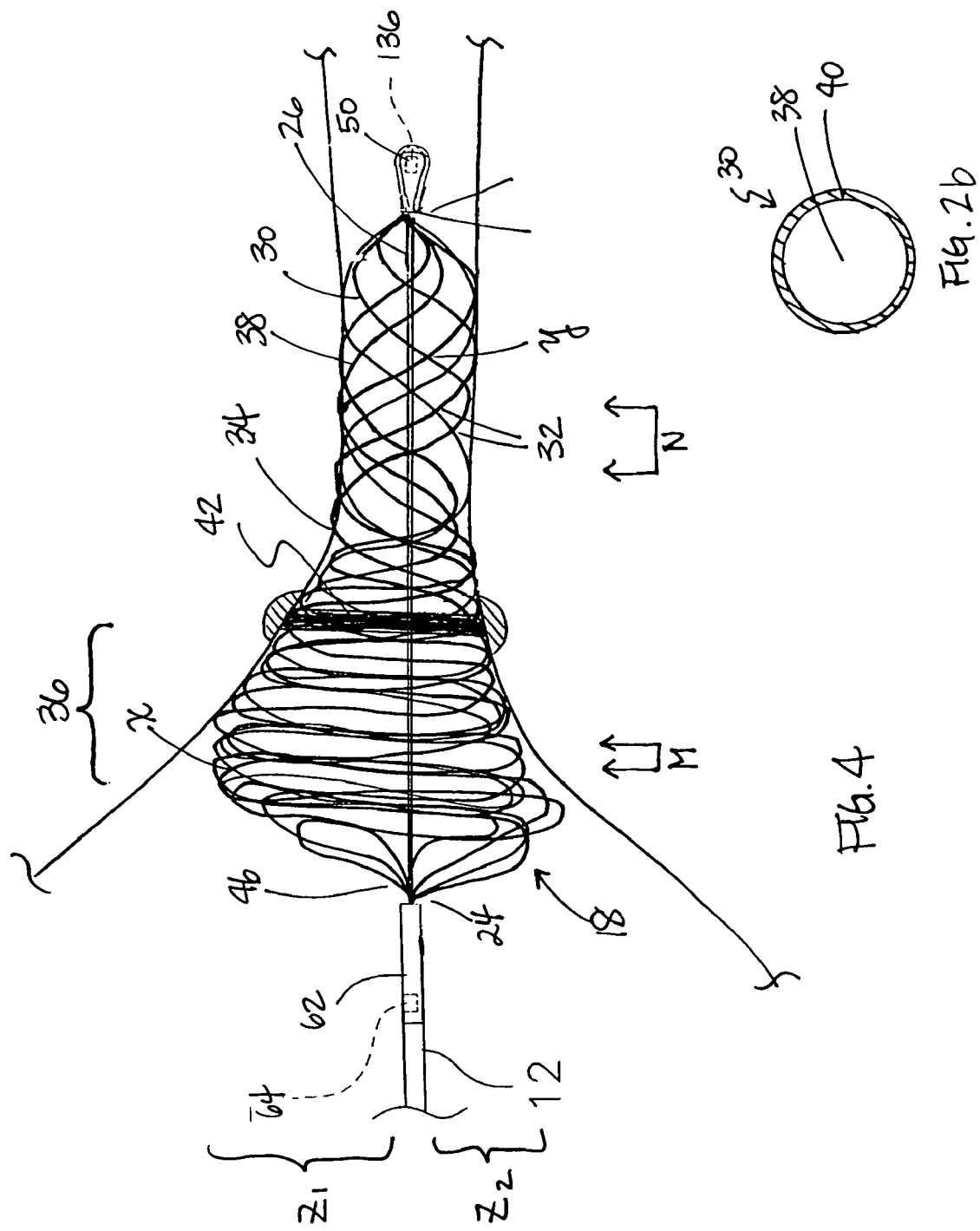

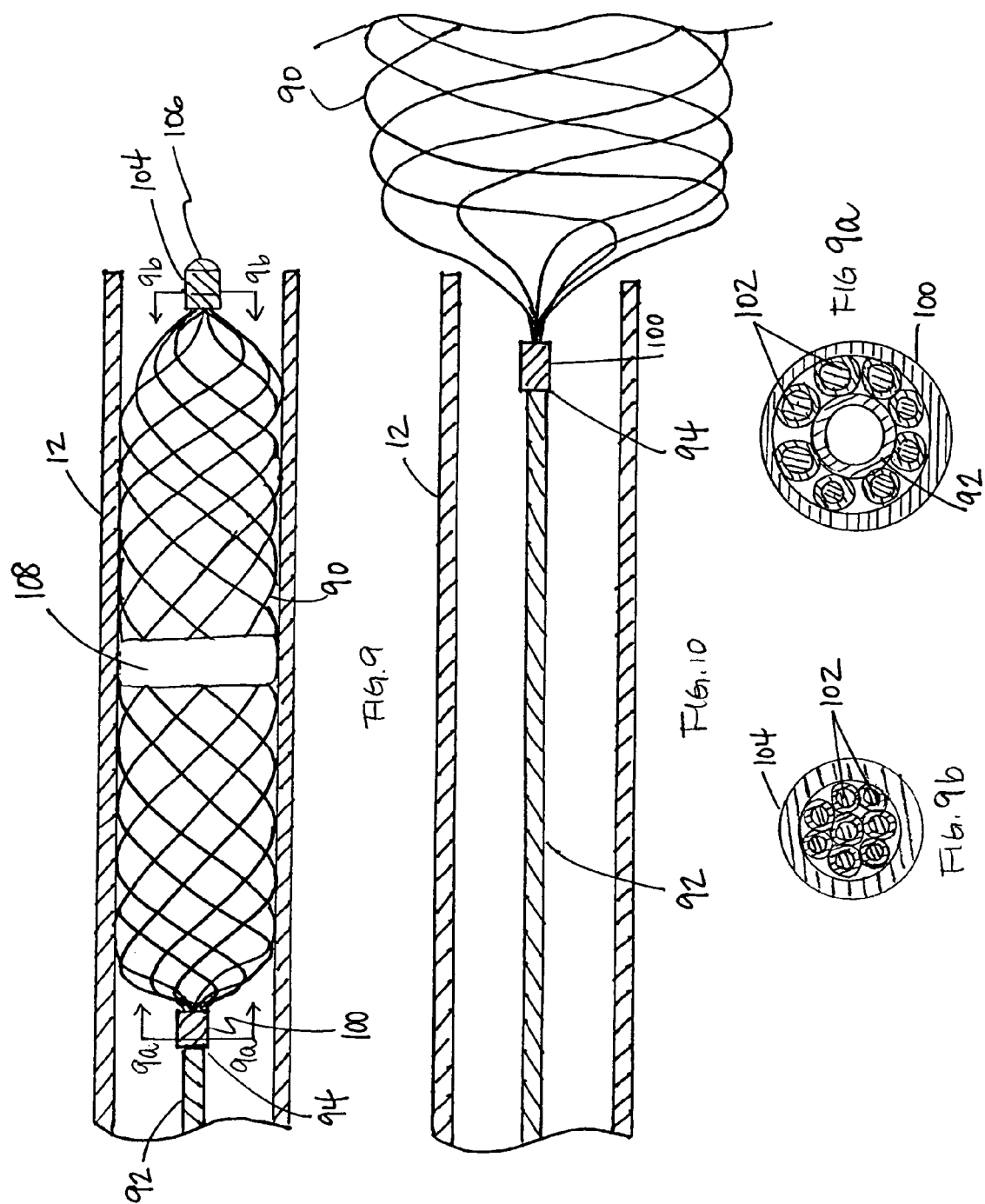

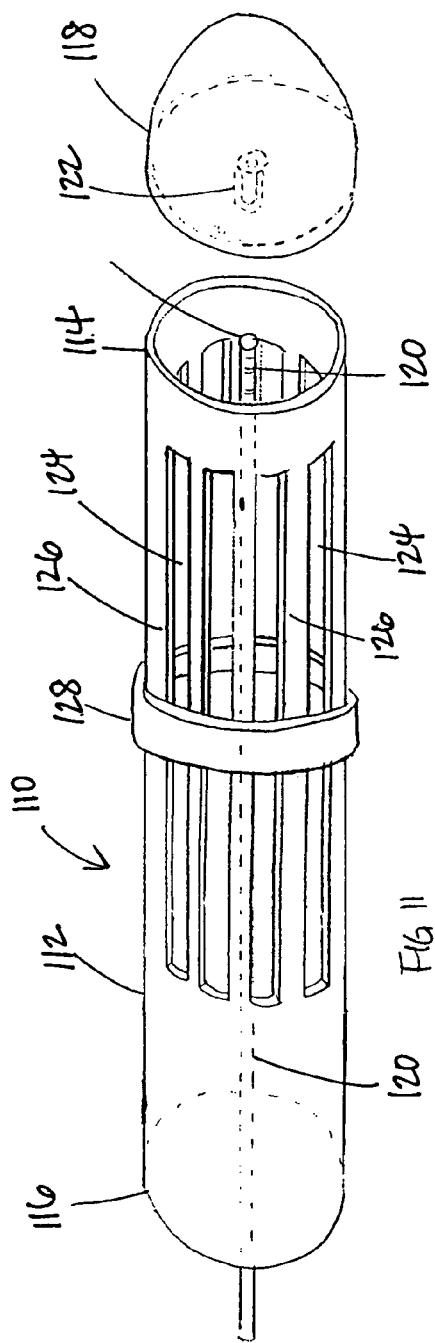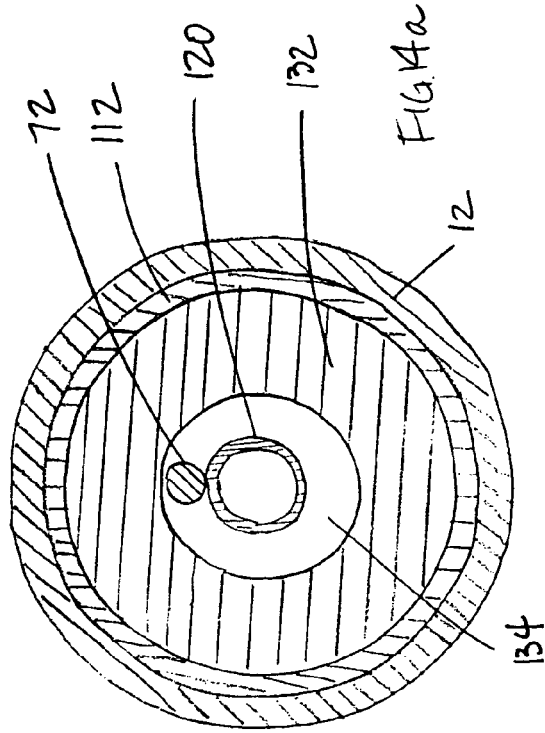

CATHETER FOR CIRCUMFERENTIAL ABLATION AT OR NEAR A PULMONARY VEIN

FIELD OF INVENTION

The present invention relates to an improved ablation catheter that is particularly useful for ablating in a tubular region in or around the heart.

BACKGROUND OF INVENTION

Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy.

A common procedure involves ablating a lesion to interrupt the wavelets using one or more electrodes mounted on the distal end of a generally-straight catheter. This procedure works well, for example, when ablating a line of block in the atria. However, for tubular regions in or around the heart, this procedure is less effective. For example, when the line of block is to be made about a circumference of the tubular region, it is difficult to manipulate and control the distal end of a straight catheter so that it effectively ablates about the circumference.

Catheters with circular ablation assemblies are known. For example, a particularly useful catheter is disclosed in U.S. Pub. No. 20030195508 (Scheib), the disclosure of which is hereby incorporated by reference. This catheter comprises a catheter body having at its distal end an ablation assembly with a preformed generally circular curve with an outer surface and being generally transverse to the axis of the catheter body. In this arrangement, the catheter has at least a portion of the outer circumference of the generally circular curve in contact with the inner circumference of a tubular region in or near the patient's heart, e.g., a pulmonary vein. However, one drawback with catheters of this type may be the relatively fixed size or circumference of the circular ablation assembly, which may not match the circumference of the tubular region undergoing treatment.

Ablation catheters with expandable assemblies are also known. Such a catheter is disclosed in U.S. Pat. No. 6,416,511 (Lesh), wherein the circumferential ablation element includes an expandable member with a working length that is adjustable from a radially collapsed position to a radially expanded position. This catheter employs an equatorial band that circumscribes the outer surface of the working length and is adapted to ablate tissue adjacent thereto when actuated by an ablation actuator. However, like most catheters with expandable members, the expandable member is a balloon structure that is inflated with a pressurized fluid source. In addition to certain complexities associated with use of a pressurized fluid source, inflation of the balloon undesirably restricts blood flow. Added complications may also arise when a balloon is forced to seat in the ostium near the treatment region, such as a pulmonary vein.

Moreover, the use of an ultrasound transducer, which often accompanies a balloon for purposes of locating or visualizing the assembly at the ostium has also caused complications because of the size of the transducer. As a relatively bulky and cumbersome accessory, the transducer can be difficult to maneuver and hamper the positioning of the balloon/transducer combination.

Also known is a basket catheter having a basket-shaped electrode array with a mechanism for expanding and retracting the electrode array, as described in U.S. application Ser. No. 10/017,564, the content of which is hereby incorporated by reference. The basket assembly has a plurality of spines connected at their proximal and distal ends to an expander that is movable longitudinally to expand and contract the basket-shaped electrode. While this assembly can accomplish circumferential ablation, it may be better suited for mapping and other diagnostic procedures in the chamber areas of the heart. Furthermore, wire spines of basket assemblies can in certain circumstances move or shift relative to each other, rendering the structure of the basket assemblies less stable than desirable.

Accordingly, a need exists for an improved catheter that is particularly useful for circumferential ablation in or near the ostium of tubular regions of the heart, especially in regions of varying or nonuniform circumference, and/or noncircular cross-sections. It is desirable that the ablation assembly has a sufficiently stable framework and that it minimizes disturbance to blood flow in the region. It is further desired that the ablation assembly be detectable by means other than through the use of ultrasound transducer which requires the application of a saline field.

SUMMARY OF THE INVENTION

The present invention is directed to a catheter with a three-dimensional, hollow ablation assembly that carries at least one ribbon electrode for circumferential ablation. The catheter comprises an elongated flexible tubular catheter body having an axis and proximal and distal ends, and an ablation assembly that is mounted at the distal end of the tubular body. The ablation assembly has a framework whose interdependent dimensions include a length and a circumference (or diameter) that readily vary and conform to a tubular volume. The framework is collapsed for passage into a tubular region at or near a patient's heart and expanded upon deployment at the treatment site to conform to the tubular region.

The framework in one embodiment is constructed of multiple tensile members or wires that are interwoven such that the length of the framework increases while the circumference of the framework decreases, and vice versa. When collapsed, the framework assumes a greater length and a lesser circumference; when expanded, the framework assumes a lesser length and a greater circumference. Each tensile member extends the length of the ablation assembly on a changing diagonal in a helical pattern about a longitudinal axis of an expander that extends through the catheter body and is movable in a longitudinal direction to expand and collapse the ablation assembly.

In one embodiment, the expander extends through the framework of the ablation assembly such that the expander forms the axis of the framework. As such, the catheter assembly may be expanded with proximal movement of the expander and collapsed with distal movement of the expander. In another embodiment, the framework is mounted on a distal end of the expander and is constructed of a material with shape memory. As such, the catheter assembly is pushed past the catheter body with distal movement of the expander for self-deployment when there is no constraint against expansion and withdrawn into the catheter body with proximal movement of the expander after ablation.

In yet another embodiment, the framework is configured from a tubular or cylindrical structure having a length and a circumference (or diameter) and whose side wall has longitudinal slots between longitudinal slats for radial expansion to a greater circumference when the length is decreased. In particular, each slat has a substantially rectangular cross-section such that deflection or bowing of the slats is predictably outwardly in the radial direction when the framework is deployed with proximal movement of the expander. As a seamless unitary structure configured by, e.g., laser cutting, this embodiment also has improved structural stability. The construction material of the tube or cylinder may also have shape-memory. In that regard, the catheter can also be configured such that the ablation assembly is withdrawn into the catheter body with proximal movement of the expander and pushed past the catheter body for deployment with distal movement of the expander.

Regardless of the embodiment of the ablation assembly and its framework, the flexible ribbon electrode carried thereon is elastic, or is pleated so that it folds when the framework is collapsed and unfolds when the framework is deployed. In either case, the ribbon electrode is held firmly against the inner circumference of the tubular region when the ablation assembly is deployed to apply a circumferential lesion. The ablation assembly therefore offers improved anchoring capabilities at the treatment site and improved contact for circumferential ablation.

In use, the catheter is fed into the patient's body through a guiding sheath. The catheter assembly remains in a collapsed configuration assuming a minimum diameter (or circumference) and a maximum length until the assembly travels past the distal end of the guiding sheath (and is pushed past the distal end of the catheter body as the case may be). With the catheter in position, such as at or near the ostium or in a pulmonary vein, the framework of the deployed assembly assumes a greater circumference in conformity with the tubular region.

The ribbon electrode may be constructed of any electrically conductive material that is also preferably detectable by X-ray and/or has shape memory. The catheter assembly may include multiple ribbon electrodes for bipolar ablation and/or for providing an electrode array with a grid-like pattern for ablation or mapping. The catheter assembly may also include a straight or deflectable tip electrode distal to the 3-D framework. As with conventional catheters, the ribbon electrode(s) and the tip electrode are energized by RF or electrical energy.

If needed, the ablation assembly is rotated so that the assembly can establish different points of contact to ensure a continuous circumferential lesion. Before the catheter assembly is retrieved from the patient's body or relocated therein, the assembly is returned to its elongated configuration and/or drawn into the guiding sheath (and the catheter body as the case may be) for better maneuvering and passage in the patient's body.

With any of the foregoing framework designs, the catheter of the present invention permits the user to have more control when ablating about a circumference of a tubular region in or around the heart, e.g., a pulmonary vein, the coronary sinus, the superior vena cava, or the pulmonary outflow tract.

BRIEF DESCRIPTION OF THE DRAWINGS

These and other features and advantages of the present invention will be better understood by reference to the following detailed description when considered in conjunction with the accompanying drawings wherein:

FIG. 1 is a perspective view of a catheter according to an embodiment of the invention.

FIG. 2 is a close-up perspective view of the ablation assembly in the deployed or expanded configuration, along with the housing, and the distal end of the catheter body of the catheter of FIG. 1.

FIG. 2b is a cross sectional view of a tensile member of the framework of the ablation assembly of FIG. 2.

FIG. 3 is a close-up perspective view of the ablation assembly in a collapsed configuration, along with the housing, and the distal end of the catheter body of the catheter of FIG. 1.

FIG. 4 is a close-up sectional view of the ablation assembly of FIG. 1 deployed within a tubular region in a patient's body.

FIG. 9 is a side cross-sectional view of an alternative embodiment of catheter of the present invention, the ablation assembly being shown withdrawn in the catheter body.

FIG. 9a is a cross-sectional view of the tubing and the distal end of the framework of FIG. 9.

FIG. 9b is a cross-sectional view of the tubing, the proximal end of the framework and the distal end of the expander.

FIG. 10 is a side cross-sectional view of the catheter of FIG. 9, the ablation assembly being shown deployed outside of the catheter body.

FIG. 11 is a close-up perspective view of another alternative embodiment of the ablation assembly of the present invention.

FIG. 14a is an end cross-sectional view of the distal end of the catheter body, the disk insert and the proximal end of the assembly of FIG. 14.

DETAILED DESCRIPTION OF THE INVENTION

The invention is directed to a catheter 10 having at its distal end a hollow, three-dimensional ablation assembly with one or more ribbon electrodes. As shown in FIG. 1, the catheter comprises an elongated catheter body 12 having proximal and distal ends, a control handle 16 at the proximal end of the catheter body, and a hollow 3-D ablation assembly 18 mounted at the distal end of the catheter body 12.

The catheter body 12 comprises an elongated tubular construction having a single, axial or central lumen (not shown), but can optionally have multiple lumens if desired. The catheter body 12 is flexible, i.e., bendable, but substantially non-compressible along its length. The catheter body 12 can be of any suitable construction and made of any suitable material. A presently preferred construction comprises an outer wall made of polyurethane or PEBAX.RTM. (polyether block amide). The outer wall comprises an imbedded braided mesh of stainless steel or the like to increase torsional stiffness of the catheter body 12 so that, when the control handle 16 is rotated, the distal end of the catheter body will rotate in a corresponding manner.

The outer diameter of the catheter body 12 is not critical, but is preferably no more than about 8 french, more preferably about 7 french. Likewise the thickness of the outer wall is not critical, but is preferably thin enough so that the central lumen can accommodate a puller wire, lead wires, sensor cables and any other wires, cables or tubes. If desired, the inner surface of the outer wall is lined with a stiffening tube (not shown) to provide improved torsional stability. An example of a catheter body construction suitable for use in connection with the present invention is described and depicted in U.S. Pat. No. 6,064,905, the disclosure of which is incorporated herein by reference.

Figure 2A:
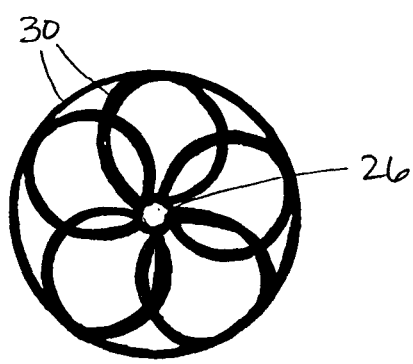
FIG. 2a is an end view of the framework of the ablation assembly of FIG. 2.
Figure 3A:
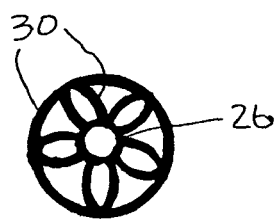
FIG. 3a is an end view of the framework of the ablation assembly of FIG. 3.

Referring to FIGS. 2-3, the assembly 18 is mounted to the distal end of the catheter body 12. In accordance with the present invention, the assembly 18 is a three-dimensional, free-form hollow or tubular framework 20 extending between a distal end 22 and a proximal end 24 that are affixed to an expander 26 such that the expander forms an axis 28 of the assembly 18.

Dimensions of the framework 20 include a circumference C (or diameter D, used interchangeably herein) and a length L that vary interdependently to each other to conform to a surrounding volume or tubular region. The terms diameter D, circumference C and the length L are loosely used herein and in a broad sense in that the framework is somewhat tubular, but it may not have a constant diameter or circumference along its length, nor a constant length along its circumference. Moreover, the circumference at any point along the length need not define a circular cross-section. That is, the cross-section could be oval, ellipsoid, or asymmetrical due to various factors, for example, abnormal tissue growth, injury, scarring or birth defect.

The framework 20 of the embodiment shown in FIGS. 2 and 3 is a mesh, free-form structure constructed of multiple tensile members 30 that are flexibly interwoven, for example, in a diamond braid pattern or other hollow braid patterns, such that the length L and the diameter D are interdependent. Each of the interwoven tensile member extends the length of the framework 20 along a changing diagonal in a helical pattern relative to the expander 26 or a longitudinal axis of the framework, such that an angle of intersection (at any node 32) between any pair of criss-crossing tensile members 30 can change with an increase in the length and/or a decrease in the diameter of the framework 20. As such, the overall framework 20 is sufficiently flexible and pliable such that the diameter D need not be constant along the length L, nor the length L along the circumference. Indeed, as shown in FIG. 4, the framework 20 is shown adopting or otherwise conforming to the interior volume of a nonuniformly-shaped tubular region 34, for example, an ostium leading to a pulmonary vein. The angle of intersection at node X differs from that at node Y. Likewise, a space or distance between adjacent wires at point M differs from that at point N. It is further noted that framework 20 may adopt asymmetric configurations, for example, along length 36 where the expander 26 is not centered within the framework (with a distance or radius Z1 being greater than a distance or radius Z2). It is also understood by one of ordinary skill in the art that the expander 26 need not extend linearly when the assembly 18 is deployed.

Despite its hollow configuration, the framework 20 is a relatively stable structure in any of its possible configurations. That is, with the catheter assembly 18 in position, an intersecting angle or a distance between intersecting or adjacent tensile member 30 is substantially maintained within the framework 20 until the framework configuration is changed or otherwise manipulated by the expander 26, as discussed further below. As such, the catheter assembly 18 offers improved anchoring capabilities and hence a more uniform circumferential lesion over conventional circumferential ablation catheters.

The tensile members 30 of the framework are all attached, directly or indirectly, to the expander 26 at their distal ends, and to the catheter body 12 at their proximal ends. As shown in FIG. 2b, each tensile member 30 comprises a flexible wire 38 with a non-conductive covering 40. It is understood by one of ordinary skill in the art that the wires 38 may have a cross-section other than the circular cross-section shown. In a preferred embodiment, the flexible wires 38 each comprise a flat Nitinol wire and the non-conductive coverings 40 each comprise a biocompatible plastic tubing, such as polyurethane or polyimide tubing. Alternatively, the tensile members 30 can be designed without the internal flexible wire 38 if a sufficiently rigid non-conductive material is used for the non-conductive covering to permit expansion of the assembly 18, so long as the tensile member has an outer surface that is non-conductive over at least a part of its surface for mounting of the ribbon electrode.

As will be recognized by one of ordinary skill in the art, the number of tensile members or wires can vary as desired depending on the particular application, so that the number of tensile members may range between about 4 and 128 wires, preferably between about 4 and 32 wires and more preferably between about 4 and 16 wires. As used herein, the term "3-D", "tubular" or "hollow" in describing the assembly is not limited to the depicted configuration, but can include other designs, such as wire frame, space frame or geodesic designs.

Also shown in FIGS. 2-4, the catheter assembly 18 carries a flexible ribbon electrode 42 for use in circumferential ablation or mapping. The ribbon electrode forms a loop outside of and around the assembly 18 by spanning the circumference of the framework 20 at a location along the length L. The electrode 42 is secured to the framework 20 at various nodes 32 along the circumference by known means, such as adhesive, glue, welding and the like.

The ribbon electrode 42 is constructed of an electrically-conductive material. Moreover, the ribbon electrode can be made of an elastic material which stretches and shrinks in accordance with the dimensions of the framework 20 (FIGS. 1 and 2). Alternatively, the ribbon electrode 42 can be made of a material with shape memory, which expands to a larger circumference when the framework is expanded, but collapses predictably into a predetermined, preformed shaped when the framework is collapsed (FIGS. 1 and 3). In either embodiment, the ribbon electrode can be straightened or bent out of its original shape upon exertion of a force and is capable of substantially returning to its original shape upon removal of the force. A particularly preferred shape-memory material is a nickel/titanium alloy. Such alloys typically comprise about 55% nickel and 45% titanium, but may comprise from about 54% to about 57% nickel with the balance being titanium. A preferred nickel/titanium alloy is nitinol, which has excellent shape memory, together with ductility, strength, corrosion resistance, electrical resistivity and temperature stability. Accordingly, any portion or slack in the shape-memory ribbon electrode 42 between the nodes 32 is preferably tucked or pleated, preferably inwardly, when the assembly 18 is collapsed (FIG. 3).

Unexpanded or collapsed circumference of the ribbon electrode may range between about 1 mm and 2 mm or in accordance with the circumference of the collapsed assembly 18. Expanded or deployed circumference of the ribbon electrode may range between about 125-260 mm, preferably between about 125-150 mm. Width of the ribbon electrode may range between about 0.0001 inches and 0.75 inches, preferably between about 0.080 inches and 0.30 inches.

The assembly 18 may provide multiple ribbon electrodes, each at a different location along the length. Whether they are elastic or have shape memory, each of the ribbon electrodes can attain a different diameter or circumference depending on the shape or configuration of the volume of the tubular region. So equipped, the catheter assembly 18 provides an electrode array with a grid-like pattern suitable for readings proximally and/or distally within the assembly region or an entire 3-D surface, regardless of any nonuniformity in the circumference of the tubular region of interest. In a mapping context, the locations identified by the array could provide information as to the cascade of electricity flowing through the heart tissue.

In accordance with the present invention, the expander 26 is moved longitudinally to elongate and shorten the ablation assembly 18, so that in the elongated configuration the framework 20 adopts a collapsed position, and in the shortened configuration the framework 20 adopts a fuller, expanded position. In the collapsed configuration, the framework 20 can have a minimum length ranging between about 0.050 inches and 0.50 inches, and a maximum length ranging between about 2.0 inches and 8.0 inches. Further in the collapsed configuration, the framework 20 can have a minimum diameter ranging between about 7 and 8 french and a maximum diameter ranging between about 12 and 14 french.

In the expanded configuration, the framework 20 can have a minimum length ranging between about 0.015 inches and 0.25 inches, and a maximum length ranging between about 1.0 inches and 4.0 inches. Further in the expanded configuration, the framework 20 can have a minimum diameter ranging between about 5 mm and 10 mm and a maximum diameter ranging between about 45 mm and 60 mm.

It is understood by one of ordinary skill in the art that the diameter of the collapsed framework 20 is dependent on factors including the diameter of any guiding sheath used with the catheter and/or the catheter body. It is also understood by one of ordinary skill in the art that the diameter of the expanded framework 20 is dependent on factors including the diameter of the tubular region undergoing treatment. To that end, the framework 20 is hollow when deployed so there is minimum disruption or impedance to blood flow in the treatment area.

Best shown in FIGS. 2-4, the expander 26 is generally coaxial with the catheter body 12. The expander 26 has a distal end 44 at the distal end 22 of the assembly 18 and a proximal end 46 extending out the distal end of the catheter body 12 and attached to the control handle 16, as will be described further below, so that the expander can be moved longitudinally relative to the catheter body 12 to thereby radially expand and contract the assembly 18. The expander 26 comprises a material sufficiently rigid to achieve this function. In a preferred embodiment, the expander 26 comprises braided polyimide tubing, i.e., tubing having inner and outer layers of polyimide with a braided stainless steel mesh therebetween, as is generally known in the art. The expander has a guidewire lumen 48 (FIGS. 5 and 6) that extends along its entire length. As will be described further below, the guidewire lumen 48 permits a guidewire to extend through the entire length of the catheter 10 for introduction of the catheter into the body.

Figure 5:
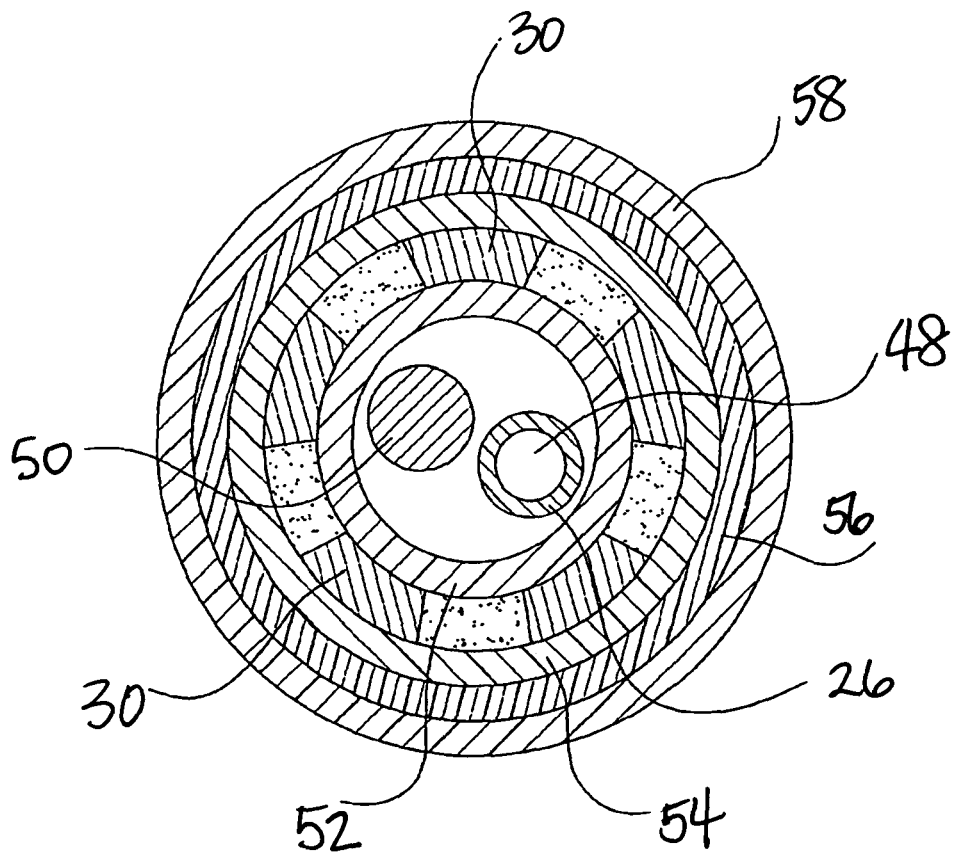
FIG. 5 is an end cross-sectional view of the housing and the distal end of the ablation assembly shown in FIGS. 2 and 3.

A preferred construction of the distal end of the assembly 18 is depicted in FIG. 5. The distal end 44 of the expander 26 and a distal location sensor 50 are held together with a first short piece of plastic, preferably polyimide, tubing 52. The distal ends of the flexible Nitinol wires 38 that form the tensile members 30 are mounted, preferably evenly-spaced, around the first piece of tubing 52. The flexible wires 38 are held in place by a second short piece of plastic, preferably polyimide, tubing 54. A generally-rigid ring 56 is then mounted around the construction over the second short piece of tubing 54 to maintain a generally round shape. The generally-rigid ring 56 can be made of metal or plastic, so long as it is sufficient rigid to achieve the above-stated function. An outer tubing 58, preferably made of polyurethane or polyimide, then covers the entire construction over the generally-rigid ring 56 so that the distal end 22 of the assembly 18 is generally atraumatic. If desired, the construction can be held together by polyurethane glue or the like. The outer tubing 58 and generally-rigid ring 56 are slightly longer than the first and second plastic tubings 52 and 54, so that the proximal ends of the outer tubing and generally-rigid ring extend beyond the proximal ends of the first and second plastic tubings. The non-conductive coverings 40 extend into the outer tubing 58 and generally-rigid ring 56, but end before the first and second plastic tubings so that only the flexible wires 38 are mounted between the first and second plastic tubings. A sensor cable 60 attached to the distal location sensor 50 extends through one of the non-conductive coverings 40 and into the distal end of the catheter body 12, as described further below. As would be recognized by one skilled in the art, other arrangements for attaching the expander 26 to the distal ends of the flexible Nitinol wires 38 and for mounting the distal location sensor 50 near the distal end of the assembly 18 could also be used in accordance with the invention.

Figure 6:
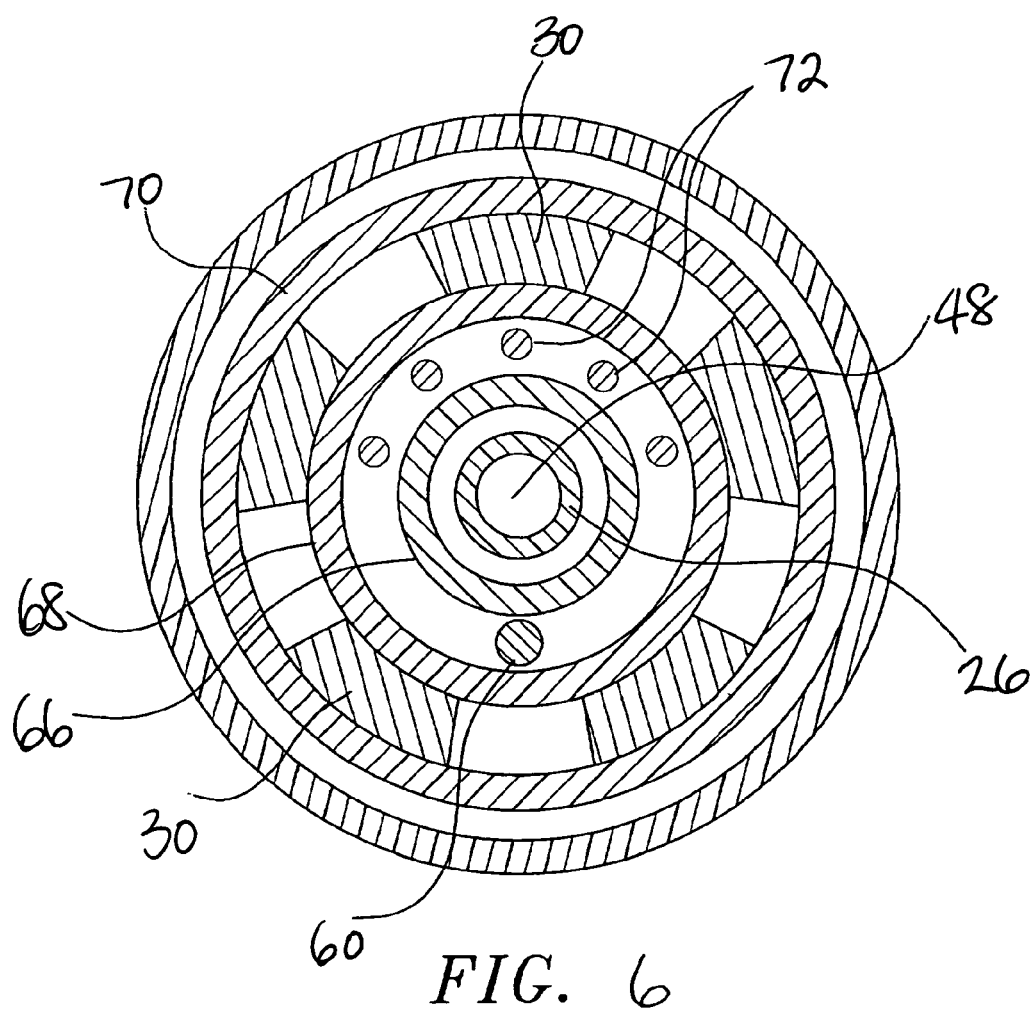
FIG. 6 is an end cross-sectional view of the housing and the distal end of the catheter body shown in FIGS. 2 and 3.
Figure 7:
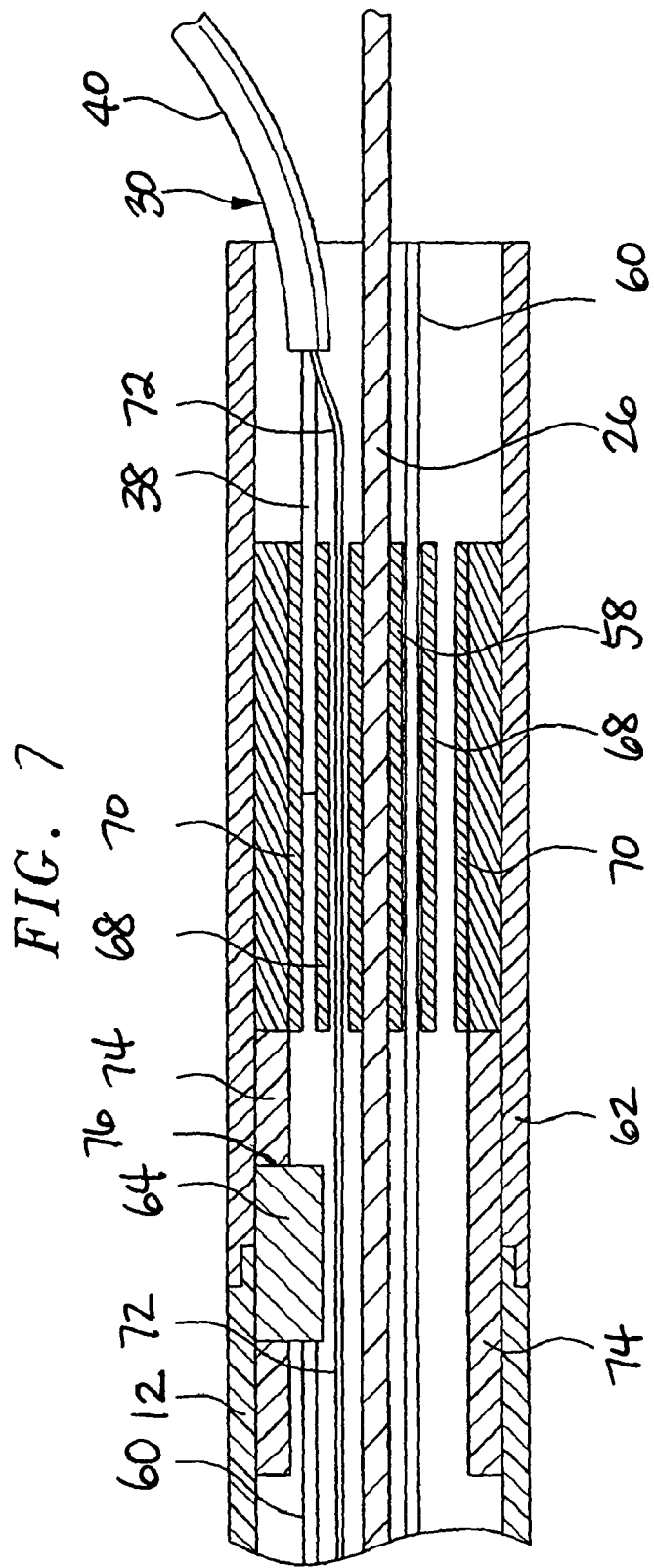
FIG. 7 is a side cross-sectional view of the housing and the distal end of the catheter body of the catheter of FIGS. 2 and 3.

A preferred construction of the proximal end of the assembly 18 and distal end of the catheter body 12 is shown in FIGS. 6 and 7. In FIG. 7, only one tensile member 30 of the assembly 18 is shown for clarity. A short plastic housing 62, preferably made of PEEK (polyether etherketone), joins the distal end of the catheter body 12 and proximal end of the assembly 18 and houses a proximal location sensor 64. Preferably, the plastic housing 62 has a length of about 11 mm. If the plastic housing 62 is too long, it can disadvantageously affect the flexibility of the distal end of the catheter body. The proximal end of the plastic housing 62 is mounted on the distal end of the catheter body 12 by any suitable method, preferably with polyurethane glue or the like.

The expander 26 must be afforded longitudinal movement within the catheter body 22. Accordingly, a tunnel 66 is formed from a piece of polyimide tubing or the like and is provided near the distal end of the catheter body 12 through which the expander 26 extends. The flexible Nitinol wires 38 are mounted, preferably evenly-spaced, between a proximal tubing 68 and an outer proximal ring 70, both of which are preferably made of polyimide, and held in place with polyurethane glue or the like. The proximal tubing 68 and outer proximal ring 70 are preferably relatively short, e.g., about 3 mm in length. Preferably electrode lead wire(s) 72 and sensor cable 60 that is attached to the distal location sensor 50 are also afforded some longitudinal movement within the catheter body 12 so that they do not break when the catheter body bends. Accordingly, in the depicted embodiment, the lead wires 72 and sensor cable 60 that is attached to the distal location sensor 50 extend within the proximal tubing 68 through which the expander 26 and tunnel 66 also extend, so that these components are not fixed in place along with the flexible Nitinol wires 38. This entire construction is mounted in the plastic housing 62. The proximal ends of the non-conductive coverings 40 of the wires 38 also extend into the plastic housing 62, but preferably end prior to the distal ends of the proximal tubing 68 and outer proximal ring 70.

The proximal location sensor 64 is also mounted within the housing 62. In the depicted embodiment, a second tunnel 74 is provided at the junction of the catheter body 12 and housing 62, with its proximal end extending into the catheter body and its distal end extending into the housing. The tunnel 74 is preferably made of polyimide and has a length ranging from about 5 to 7 mm. The tunnel 74 protects the expander 26, electrode lead wires 72 and sensor cable 60 that is attached to the distal location sensor 50 from being glued to the catheter at the junction of the catheter body and housing during assembly. Prior to assembly, the proximal location sensor 64 is mounted in a window 76 of the second tunnel 74. The proximal location sensor 64 preferably has a length of about 1 to 3 mm. The sensor cable 60 attached to the proximal location sensor 64 extends through the second tunnel 74 and catheter body 12 along with the other components. Accordingly, all of these components are afforded longitudinal movement at the junction of the catheter body 12 and the housing 62.

It is understood by one of ordinary skill in the art that the proximal end and/or distal ends of the tensile members may be movable within the tubing 54 and the ring 70 (for example, with the use of ball-bearings), where it is desired that the framework 20 be able to tighten or loosen the coils of the tensile members 30 with longitudinal movement of the expander 26. With such movement capability in the tensile members, the number of windings or coils of each tensile member about the expander can change as the expander moves longitudinally.

Figure 8:
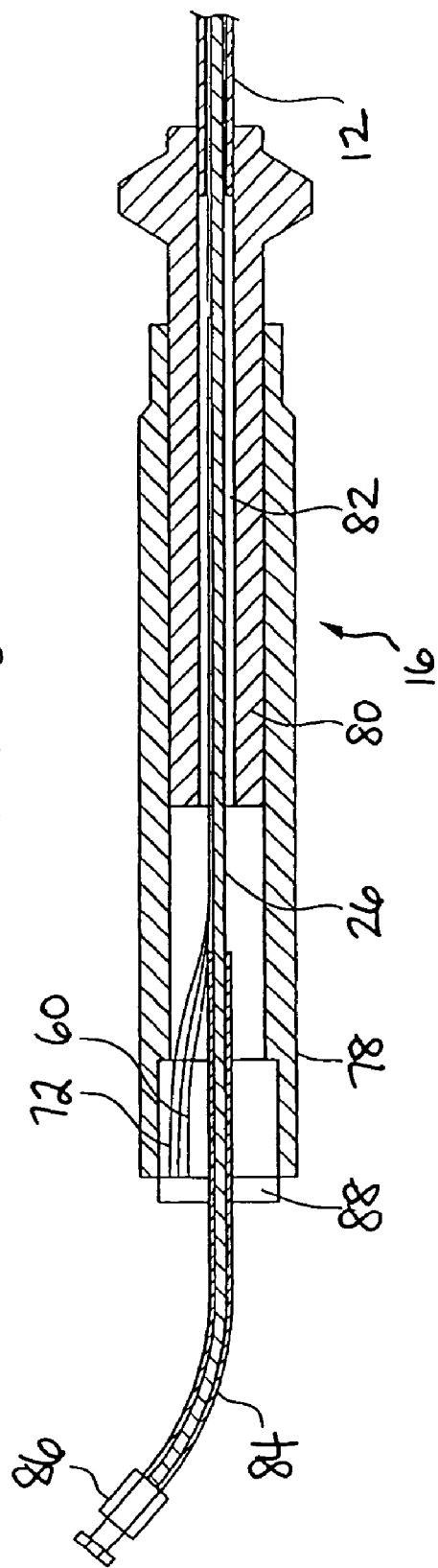
FIG. 8 is a side cross-sectional view of the control handle and the proximal end of the catheter body of the catheter of FIG. 1.

Longitudinal movement of the expander 26 distally the catheter body 12, which results in elongation of the assembly 18, is accomplished by manipulation of the control handle 16. As shown in FIG. 8, the control handle 16 comprises a generally-hollow handle housing 78 and a piston 80 slidably mounted within the distal end of the handle housing. The proximal end of the catheter body 12 is fixedly attached to the distal end of the piston 80 by a shrink sleeve (not shown), as is generally known in the art, or by any other suitable method.

Within the control handle 16, the proximal end of the expander 26 extends through a passage 82 in the piston 80, through the handle housing 78 and into a support tube 84, preferably made of braided polyimide or PEBAX.RTM. The support tube 84 extends out the proximal end of the control handle 16 and terminates in a luer hub 86. The support tube 84 and expander 26 are together fixedly attached to the handle housing 78 by any suitable method, preferably with polyurethane glue or the like. The guidewire lumen 48 of the expander 26 can also be used for infusion of fluids through the catheter, as is generally known in the art.

In a preferred embodiment, the piston 80 is approximately about 2 inches long, and the support tube 84 and expander 26 are attached to the handle housing 78 at a position about 0.5 inch distal to the proximal end of the handle and about 1 inch proximal to the proximal end of the piston in the neutral position. The piston is in the neutral position when the assembly 18 is generally collapsed, i.e., not expanded.

The lead wires 72 and sensor cables 60 also extend through the piston passage 82 and handle housing 78 and are attached to a suitable connector 88 at the proximal end of the handle housing. Alternatively, the lead wires 72 and sensor cables 60 can extend through protective support tubes (not shown), similar to the support tube 84 that carries the expander 26, which have distal ends inside the handle housing 78 and proximal ends attached to appropriate connectors.

To use the catheter of the invention, an electrophysiologist introduces a guiding sheath, guidewire and dilator into the patient, as is generally known in the art. A suitable guiding sheath for use in connection with the inventive catheter is the PREFACE.TM. Braided Guiding Sheath (commercially available from Biosense Webster, Inc., Diamond Bar, Calif.). The dilator is removed, and the catheter is introduced through the guiding sheath whereby the guidewire lumen 48 in the expander 36 permits the catheter 10 to pass over the guidewire. The guiding sheath covers the framework 20 of the assembly 18 internally in a collapsed position so that the entire catheter can be passed down a vein or artery to a desired location. Once the distal end of the catheter reaches the desired location, the guiding sheath is withdrawn. The expander 26 is then manipulated so that the length of the framework is shortened and framework expands outwardly into an expanded arrangement. In such an arrangement the tensile members 30 and/or the ribbon 42 contact the tissue of the tubular region. As will be recognized by one skilled in the art, the assembly 18 can be fully or partially expanded in a variety of configurations depending on the configuration of the region of the heart being mapped. As mentioned in reference to FIG. 4, the assembly can conform to a tubular region with a nonuniform diameter.

With reference to FIGS. 9 and 10, an alternate embodiment of the ablation assembly 18 employs a self-expanding framework 90 that is mounted on an expander 92. The expander 92 is similar to the expander 26, except that the framework 90 is mounted on a distal end 94 of the expander 92. The expander 92 is provided with the same longitudinal movement as the expander 26 but the movement is for purposes of drawing or pulling the assembly back into the catheter body 12 for passage in the patient's body and for pushing the assembly beyond the catheter body 12 for ablation. Because the framework 90 in this embodiment is constructed of shape memory tensile members 96, which may be covered by a nonconducting cover 98, the framework self-deploys when there is no constraint against expansion, such as when it is beyond the distal end of the catheter body 12.

As shown in FIG. 9a, an outer ring 100 joins the distal end 94 of the expander 92 and the proximal end of the framework 90. Tensile members 102, preferably flexible Nitinol wires, are mounted, preferably evenly-spaced, between the expander 92 and the outer ring 100. As show in FIG. 9b, at the distal end of the framework 90, a tubing 104 is affixed to and surrounds the distal ends of the tensile members 102. The tubing 104 is capped off by a cap or dome 106 (FIG. 9) for a generally atraumatic configuration.

The framework 90 has at least one flexible ribbon electrode 108 which may be elastic, or is folded when the assembly is collapsed and unfolded when the assembly is expanded. The ribbon electrode may be of Nitinol.

Figure 12A:
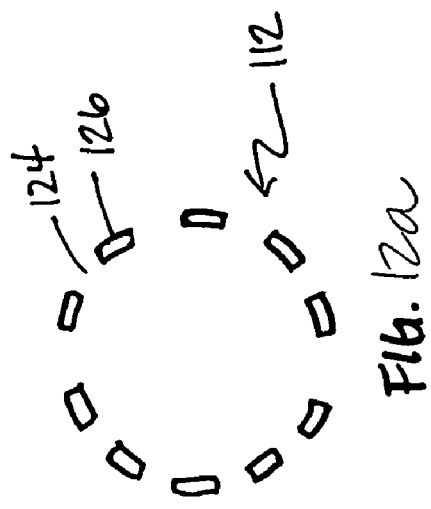
FIG. 12a is a cross sectional view of the cylinder structure of the ablation assembly of FIG. 12.
Figure 12:
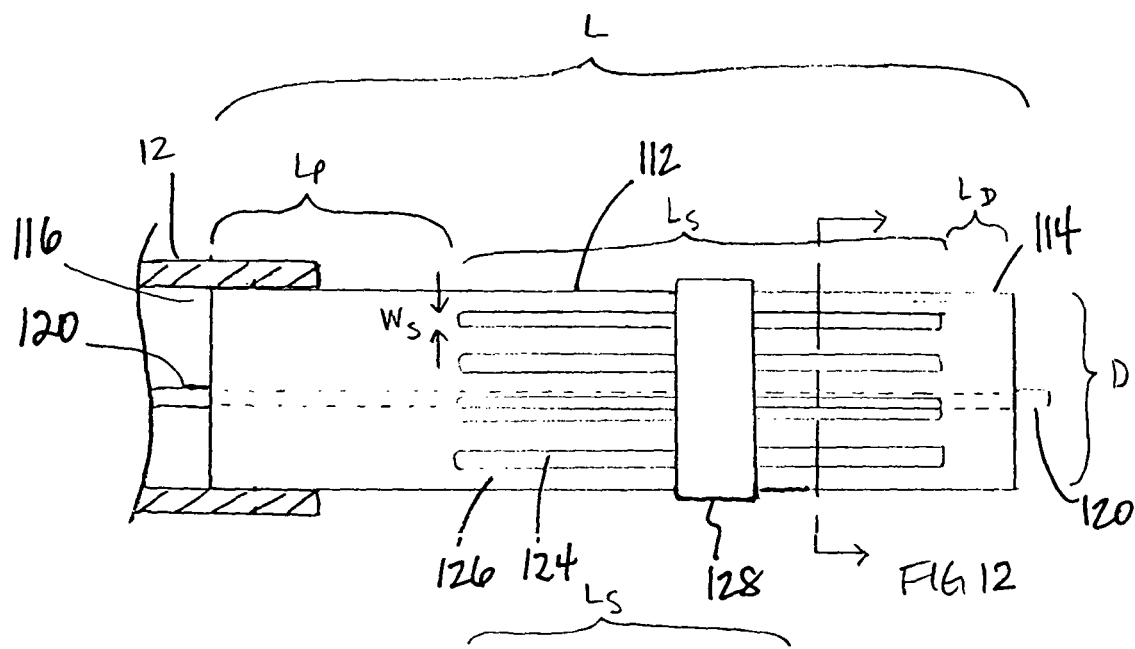
FIG. 12 is a close-up perspective view of the ablation assembly of FIG. 11.
Figure 13:
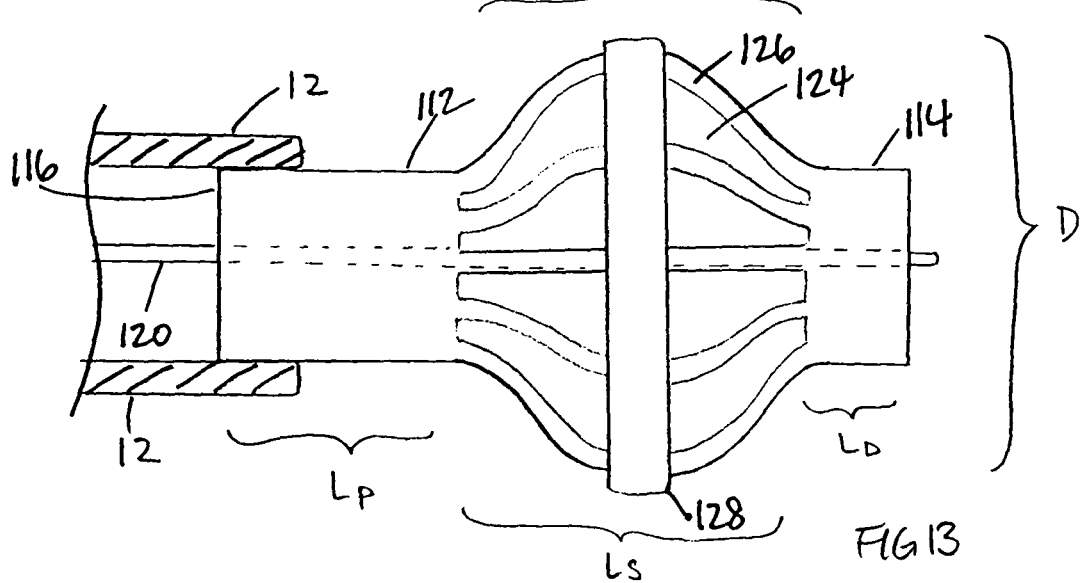
FIG. 13 is a close-up perspective view of the ablation assembly of FIG. 12 in the expanded configuration.

Another alternative embodiment of the ablation assembly 18 is shown in FIGS. 11, 12 and 13. A framework 110 is formed from a tube or cylinder structure 112 with a diameter (or circumference) D and a length L between a distal end 114 and a proximal end 116. A dome tip or cap 118 is mounted on the distal end 114 of the cylinder 112 to render the end 114 generally atraumatic. Moreover, the cap 118 provides structural support to the end 114 and also enables an expander 120 to decrease the length of the cylinder 112 for deployment, as discussed below. Extending longitudinally from a proximal end of the cap 118 is a stem 122 for receiving the distal end of the expander 120 which is glued or otherwise fixedly secured to the stem.

The structure 112 is advantageously seamless as having been laser-cut with multiple longitudinal slots 124 to form longitudinal slats 126 which (due at least in part to their rectangular cross sections, see FIG. 12a) predictably bow outwardly in the radial direction to a greater diameter (or circumference) with a decrease in the length L (FIG. 13). In the depicted embodiment, the slots 124 and slats 126 are longitudinally aligned within and limited to the length Ls which extends between a length Lp at the proximal end 116 and a length Ld at the distal end 114. Accordingly, it is the length Ls that decreases as the expander 120 is moved proximally in the longitudinal direction.

In accordance with the present invention, a ribbon electrode 128 (whether elastic or pleated) mounted circumferentially on the slats 126 at a location within the length Ls follows the expansion of the structure 112 at deployment (FIG. 13) and the collapse of the structure 112 when drawn back into the guiding sheath (FIG. 12).

It is understood by one of ordinary skill in the art that the slots 124 may be merely slits or cuts (that is, with minimal or no effective width dimension) and that the number of slots or slats can range between about 3 and 100, preferably about 5 and 25 and more preferably about 12. Moreover, the length Ls and the width Ws of each slot or slat can vary, or the slots and slats can be out of longitudinal alignment with other slots or slats. The structure 112 may also be constructed out of Nitinol, or any other material with suitable strength and flexibility.

Figure 14:
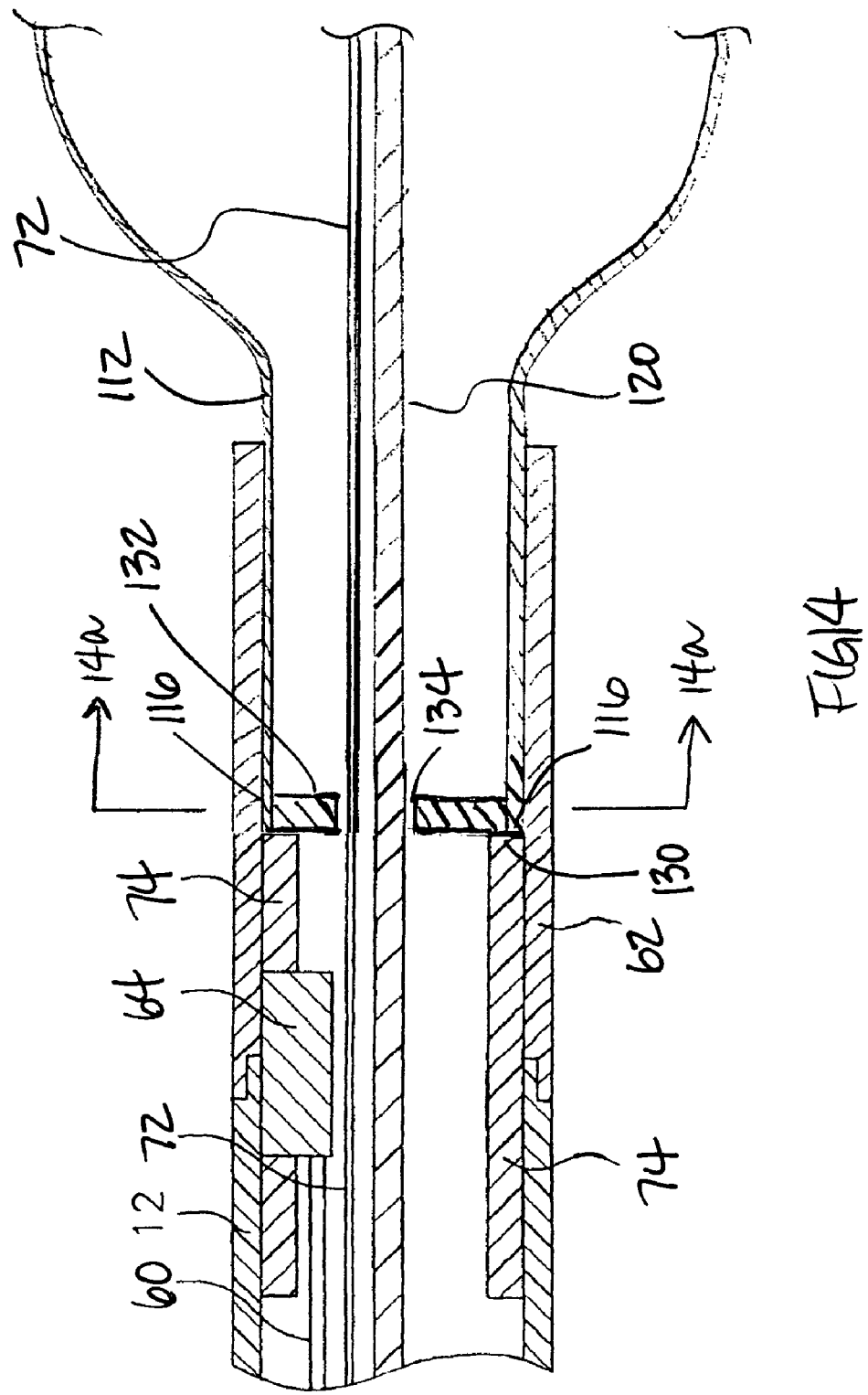
FIG. 14 is a side cross-sectional view of the housing and the distal end of the catheter body shown in FIG. 13.

FIGS. 14 and 14a, show a preferred construction of the proximal end of the ablation assembly of FIGS. 11-13 and a distal end of the catheter body 12. The short plastic housing 62 joins the distal end of the catheter body 12 and the proximal end 116 of the cylinder 112. To that end, as shown in FIGS. 12 and 13, the length Lp may be greater than the length Ld to provide sufficient contact surface between the cylinder 112 and the housing 62. Because the tunnel 74 is fixedly attached to the housing 62 and the catheter body, it anchors the proximal end 116 of the cylinder 112 which abuts its distal end 130 such that proximal movement of the expander 120 accomplishes a decrease in the length L (or, namely, the length Ls) to deploy the ablation assembly.

Also abutting the distal end 130 of the tunnel 74 is a disk insert 132 that is fitted to sit within the proximal end 116 of the cylinder 112. The disk 132 is configured with an aperture 134 through which the expander 120 and any lead wire(s) 72 extend and are afforded longitudinal movement.

The catheter 10 may also include a tip electrode 136 mounted at the distal end of the ablation assembly 18 for ablating tissue. The tip electrode can be mounted on the distal end of the framework 20 (FIG. 2), the cap 106 of the framework 90 (FIG. 9) or on the dome 118 of the framework (FIG. 11).

In addition to circumferential ablation, where the catheter 10 carries multiple ribbon electrodes along with the distal end proximal location sensors, an electrophysiologist can map local activation time, which can guide the electrophysiologist in providing therapy to the patient. The catheter can include one or more reference ring electrodes mounted on the catheter body 12, or one or more reference electrodes can be placed outside the body of the patient. By using the inventive catheter with the multiple electrodes on the assembly 18, the electrophysiologist can obtain a true anatomy of the heart by measuring less points than with traditional catheters, allowing him to map the heart more quickly. Moreover, by introducing the assembly 18 over the guidewire, the electrophysiologist can remove the catheter from the heart and later reintroduce the assembly to the same position after therapy, thereby permitting the electrophysiologist to accurately view the results of the therapy. Prior basket catheter designs did not permit this reproducibility.

If desired the catheter can include a steering mechanism for deflection of the distal end of the catheter body 12. With such a design, the distal end of the catheter body 12 preferably comprises a short length of tubing, e.g., 2 to 4 inches, that is more flexible that the remainder of the catheter body. A suitable steering mechanism comprises a puller wire (not shown) that extends from a proximal end in the handle through the catheter body and into an off axis lumen in the catheter tip section. Within the catheter body, the puller wire extends through a closely wound coil that is bendable but substantially compressible. The coil is fixed near the proximal and distal ends of the catheter body and prevents deflection of the catheter body. The distal end of the puller wire is anchored at the distal end of the catheter body proximal to the proximal end of the basket. The proximal end of the puller wire is anchored to a movable member in the handle that can be moved relative to the catheter body. Proximal movement of the movable member relative to the catheter body results in deflection of the catheter tip section. An example of such a steering mechanism and construction is described in more detail in U.S. Pat. No. 6,064,905, the disclosure of which is incorporated herein by reference.

If a steering mechanism is included, the control handle 16 may be of any suitable construction for manipulating two wires, in this case, the expander and a puller wire. Preferably the handle has a pair of movable members to which the expander and puller wire attach, such as handles typically used for bidirectional and multidirectional catheters. Examples of such handles are disclosed in U.S. Pat. Nos. 6,210,407, 6,198,974, 6,183,463, 6,183,435, 6,171,277, and 6,123,699, the disclosures of which are incorporated herein by reference.

Suitable deflection control handles for use with such a catheter are described in U.S. patent application Ser. No. 08/924,611, filed Sep. 5, 1997, entitled "Omni-Directional Steerable Catheter", 09/130,359, filed Aug. 7, 1998, entitled "Bi-Directional Control Handle for Steerable Catheter", and 09/143,426, filed Aug. 28, 1998, entitled "Bidirectional Steerable Catheter with Bidirectional Control Handle", and U.S. patent application entitled "Single Gear Drive Bidirectional Control Handle for Steerable Catheter" to Tim Bumbalough, et al., filed Apr. 10, 2000, the disclosures of which are incorporated herein by reference.

In an alternative embodiment (not shown), the tensile members do not include non-conductive coverings so that the flexible Nitinol wires each act as an elongated electrode, obviating the ribbon electrode. In such an embodiment, the sensor cable attached to the distal location sensor can extend through a second lumen (not shown) in the expander. Electrode lead wires can then be attached to the proximal ends of the tensile members within the catheter body. As would be recognized by one skilled in the art, other electrode configurations on the assembly 18 could also be used in accordance with the invention.

In another alternative embodiment (not shown), the catheter does not include a control handle. In such an embodiment, the proximal end of the expander will extend out the proximal end of the catheter body and can be manipulated directly. However, such a design may be less desirable from a practical standpoint, as it may be more difficult for the electrophysiologist to control.

The preceding description has been presented with references to presently preferred embodiments of the invention. Persons skilled in the art and technology to which this invention pertains will appreciate that alterations and changes in the described structures can be practiced without meaningfully departing from the principle, spirit and scope of this invention. For example, the different embodiments of the ablation assembly can be used with any of the different embodiments of the expander, and vice versa. Moreover, the different methods and structures described for attaching, connecting or otherwise joining the ends of the expander and the tensile members of the frameworks can be interchanged as desired. Furthermore, all of the dimensions described herein are approximations. Accordingly, the foregoing description should not be read as pertaining only to the precise structures described and shown in the accompanying drawings (which may not be to scale), but rather should be read as consistent with and as support for the following claims, which are to have their fullest and fairest scope.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
    an elongated catheter body having proximal and distal ends and at least one lumen therethrough;
    a three-dimensional ablation assembly at or near the distal end of the catheter body, said assembly having a framework defining a length and a circumference, the assembly movable into a collapsed configuration with a greater length and a lesser circumference and an expanded configuration with a lesser length and a greater circumference, the framework comprising a plurality of tensile members interwoven in a manner such that the length increases as the circumference decreases and vice versa, the tensile members having proximal ends mounted between a proximal tubing and an outer proximal ring, and wherein the expanded configuration of the framework has a variable shape that changes to conform to nonuniformly shaped tubular regions;
    said assembly also having a ribbon electrode extending along said circumference, said ribbon electrode adapted to move with said framework;
    a first electrode lead wire connected to the ribbon electrode;
    a tip electrode mounted at or near a distal end of the ablation assembly;
    a second electrode lead wire connected to the tip electrode; and
    an expander attached to the tensile members and extending through at least the distal end of the catheter body, whereby, in use, the expander can be moved longitudinally relative to the catheter body to expand and collapse the assembly, wherein a portion of the expander extending through the distal end of the catheter body extends through a first tubing within the proximal tubing in the distal end of the catheter body, and the first and second electrode lead wires extend between the first tubing and the proximal tubing.

2. A catheter of claim 1, wherein said framework of the assembly in the expanded configuration has a first circumference in a first section along its length and a different second circumference in a second section along its length.

3. A catheter of claim 1, wherein the expander is attached at or near its distal end to distal ends of the tensile members and extends through the catheter body, the expander having a proximal end that extends out the proximal end of the catheter body, and having a lumen extending therethrough.

4. The catheter of claim 3, wherein the expander comprises plastic tubing.

5. The catheter of claim 3, wherein the expander comprises braided plastic tubing.

6. The catheter of claim 3, wherein the expander has a proximal end attached to a control handle.

7. The catheter of claim 6, wherein the control handle comprises:
    a handle housing having proximal and distal ends, and a piston having a proximal end mounted in the distal end of the handle housing and a distal end fixedly attached to the proximal end of the catheter body;
    wherein the proximal end of the expander is fixedly attached, directly or indirectly, to the handle housing so that longitudinal movement of the piston relative to the handle housing results in longitudinal movement of the expander relative to the catheter body to thereby expand and collapse the assembly.

8. The catheter of claim 7, wherein the proximal end of the expander extends outside the proximal end of the control handle and through a support tube.

9. The catheter of claim 3, wherein the expander is generally coaxial with the catheter body.

10. The catheter of claim 3, wherein the expander forms the axis of the assembly.

11. A catheter of claim 1, wherein the expander is attached at or near its distal end to distal ends of the tensile members.

12. A catheter of claim 1, wherein the expander is moved proximally to actuate the assembly into the expanded configuration.

13. The catheter of claim 1, wherein the assembly comprises at least four tensile members.

14. The catheter of claim 1, wherein each tensile member comprises an internal flexible wire and a non-conductive covering over the flexible wire.

15. The catheter of claim 14, wherein the internal flexible wire of each wire comprises nitinol.

16. The catheter of claim 1, wherein the ribbon electrode is elastic.

17. A catheter of claim 1, wherein the ribbon electrode comprises a plurality of ribbon electrodes, each ribbon electrode extending along a circumference of the framework and being adapted to move with the framework.

18. A catheter of claim 1, wherein when the ablation assembly is in the collapsed configuration, portions of the ribbon electrode are tucked inward between the tensile members.

19. A catheter of claim 1, further comprising a proximal location sensor mounted proximal the ablation assembly, and a distal location sensor mounted distal the ablation assembly.

20. A catheter comprising:
    an elongated catheter body having proximal and distal ends and at least one lumen therethrough;
    a three-dimensional ablation assembly at or near the distal end of the catheter body, said assembly having a framework defining a length and a circumference, the assembly being movable into a collapsed configuration having a greater length and a lesser circumference and an expanded configuration having a lesser length and a greater circumference, the framework comprising a plurality of tensile members interwoven in a manner such that the length increases as the circumference decreases and vice versa, the tensile members having proximal ends mounted between a proximal tubing and an outer proximal ring, and wherein the framework is sufficiently flexible that the diameter need not be constant along the length and the length need not be constant along the circumference so that the expanded configuration of the framework has a variable shape that changes to conform to differently shaped interior volumes of nonuniformly-shaped tubular regions;

said assembly also having a ribbon electrode extending along said circumference, said ribbon electrode adapted to move with said framework;

an electrode lead wire connected to the ribbon electrode; and an expander attached to the tensile members and extending through at least the distal end of the catheter body, whereby, in use, the expander can be moved longitudinally relative to the catheter body to expand and collapse the assembly, wherein a portion of the expander extending through the distal end of the catheter body extends through a first tubing within the proximal tubing in the distal end of the catheter body, and the electrode lead wire extends between the first tubing and the proximal tubing.

21. A catheter of claim 20, wherein the ribbon electrode comprises a plurality of ribbon electrodes, each ribbon electrode extending along a circumference of the framework and being adapted to move with the framework.

22. A catheter of claim 20, wherein when the ablation assembly is in the collapsed configuration, portions of the ribbon electrode are tucked inward between the tensile members.

23. A catheter of claim 20, further comprising a proximal location sensor mounted proximal the ablation assembly, and a distal location sensor mounted distal the ablation assembly.

24. A catheter comprising:

an elongated catheter body having proximal and distal ends and at least one lumen therethrough;

a three-dimensional ablation assembly at or near the distal end of the catheter body, said assembly having a framework defining a length and a circumference, the assembly movable into a collapsed configuration with a greater length and a lesser circumference and an expanded configuration with a lesser length and a greater circumference, the framework comprising a plurality of tensile members interwoven in a manner such that the length increases as the circumference decreases and vice versa, the tensile members having proximal ends mounted between a proximal tubing and an outer proximal ring, and wherein the expanded configuration of the framework has a variable shape in which the length and circumference vary interdependently to each other to conform to differently shaped surrounding volumes;

said assembly also having a ribbon electrode extending along said circumference, said ribbon electrode adapted to move with said framework;

an electrode lead wire connected to the ribbon electrode; and an expander attached to the tensile members and extending through at least the distal end of the catheter body, whereby, in use, the expander can be moved longitudinally relative to the catheter body to expand and collapse the assembly, wherein a portion of the expander extending through the distal end of the catheter body extends through a first tubing within the proximal tubing in the distal end of the catheter body, and the electrode lead wire extends between the first tubing and the proximal tubing.

* * * * *